(12) United States Patent
Jerebko et al.

(10) Patent No.: US 9,962,129 B2
(45) Date of Patent: May 8, 2018

(54) METHOD AND APPARATUSES FOR ASSISTING A DIAGNOSING PRACTITIONER WITH DESCRIBING THE LOCATION OF A TARGET STRUCTURE IN A BREAST

(71) Applicant: SIEMENS HEALTHCARE GMBH, Erlangen (DE)

(72) Inventors: Anna Jerebko, Hausen (DE); Michael Kelm, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 1 day.

(21) Appl. No.: 15/347,248

(22) Filed: Nov. 9, 2016

(65) Prior Publication Data

US 2017/0132792 A1 May 11, 2017

(30) Foreign Application Priority Data

Nov. 9, 2015 (DE) .................. 10 2015 221 998

(51) Int. Cl.
*G06K 9/00* (2006.01)
*A61B 6/02* (2006.01)
(Continued)

(52) U.S. Cl.
CPC .............. *A61B 6/025* (2013.01); *A61B 6/461* (2013.01); *A61B 6/467* (2013.01); *A61B 6/502* (2013.01);
(Continued)

(58) Field of Classification Search
CPC ..... A61B 5/0536; A61B 5/1077; A61B 6/502; A61B 5/0064; A61B 5/05
(Continued)

(56) References Cited

U.S. PATENT DOCUMENTS 7,627,362 B2 * 12/2009 Gregory ............... A61B 5/0064
600/427
7,634,049 B2 * 12/2009 Galkin ................. A61B 6/0414
378/37
(Continued)

FOREIGN PATENT DOCUMENTS

| DE | 102010063810 A1 | 6/2012 |
| EP | 2634748 A1 | 9/2013 |
| EP | 2693400 A2 | 2/2014 |

OTHER PUBLICATIONS

Sofka, M. et al.: "Integrated Detection Network (IDN) for pose and boundary estimation in medical images" IEEE, Int. Symp. Biomed. Imag.: Nano to Macro, Chicago, IL, USA. (Mar. 2011) 294-299.
(Continued)

*Primary Examiner* — Charlotte M Baker
(74) *Attorney, Agent, or Firm* — Laurence Greenberg; Werner Stemer; Ralph Locher

(57) ABSTRACT

An operating method assists a diagnosing practitioner with describing the location of a target structure in a tomosynthesis image data record of a compressed breast of a patient. The target structure is localized by a first spatial information item. The method includes: a) ascertaining a first shape information item describing at least one first, compressed breast shape in the tomosynthesis image data record, b) determining a second shape information item describing the breast in a non-compressed breast shape, from the first shape information item, c) mapping the position of the target structure from the compressed breast shape and to the non-compressed breast shape using at least the second shape information item for ascertaining a second spatial information item relating to the non-compressed breast shape, and d) transforming the second spatial information item into a pictogram information item facilitating an abstracted pictorial representation and/or describing the latter.

26 Claims, 4 Drawing Sheets

(51) Int. Cl.
*A61B 6/00* (2006.01)
*G06T 7/00* (2017.01)

(52) U.S. Cl.
CPC .......... *A61B 6/5217* (2013.01); *G06T 7/0081* (2013.01); *G06T 2207/10112* (2013.01); *G06T 2207/30068* (2013.01)

(58) Field of Classification Search
USPC .......... 382/128, 132; 378/37; 600/427, 478, 600/509, 547
See application file for complete search history.

(56) References Cited

U.S. PATENT DOCUMENTS

| | | |
|---|---|---|
| 9,235,888 B2 | 1/2016 | Jerebko et al. |
| 9,668,711 B2 * | 6/2017 | Smith .................... A61B 6/025 |
| 2002/0154802 A1 * | 10/2002 | Goldkuhl ................. G06T 5/50 |
| | | 382/132 |
| 2012/0157819 A1 | 6/2012 | Jerebko et al. |

OTHER PUBLICATIONS

Zonderland, H. et al.: "Bi-RADS for Mammography and Ultrasound 2013" The Radiology Assistant Updated version, 2013.
Zheng, Y. et al, "Four-Chamber Heart Modeling and Automatic Segmentation for 3-D Cardiac CT Volumes Using Marginal Space Learning and Steerable Features", IEEE Transactions on Medical Imaging vol. 27, No. 11, pp. 1668-1681, 2008.

* cited by examiner

METHOD AND APPARATUSES FOR ASSISTING A DIAGNOSING PRACTITIONER WITH DESCRIBING THE LOCATION OF A TARGET STRUCTURE IN A BREAST

CROSS-REFERENCE TO RELATED APPLICATION

This application claims the priority, under 35 U.S.C. § 119, of German application DE 10 2015 221 998.4, filed Nov. 9, 2015; the prior application is herewith incorporated by reference in its entirety.

BACKGROUND OF THE INVENTION

Field of the Invention

The invention relates to a method, an apparatus and a computer program for assisting a diagnosing practitioner with describing the location of at least one target structure localized in a tomosynthesis image data record of a compressed breast of a patient, the target structure being described by a first spatial information item.

Malignant changes to the breast constitute a health problem for many patients. Since this not only relates to female patients, counter to public perception, reference is made below to a patient in general rather than a female patient. Here, two-dimensional mammography is often used for screening or diagnostic assessment. However, in recent times, the two-dimensional mammography is being replaced ever more frequently by digital breast tomosynthesis (DBT), in particular for differential diagnoses. However, the use of DBT has already been proposed for screening for breast cancer.

In DBT, a plurality of two-dimensional projection images are recorded from different projection directions, i.e. from different projection angles. Using reconstruction methods employing concepts from computed tomography, it is possible to obtain three-dimensional tomosynthesis image data records which allow an improved spatial localization of target structures, in particular suspect lesions. Like in the two-dimensional tomography as well, it is usual for the breast to be recorded to be compressed by a compression plate ("paddle") for the recording, as is well known in the prior art. It is also possible to use usual views within the scope of DBT, with the corresponding viewing direction ultimately forming the center point for the varying projection directions. By way of example, it is known to carry out both mediolateral-oblique (MLO) scans and cranial-caudal scans (CC scans). Here, provision is often made for the breast to be compressed in different ways. If a tomosynthesis image data record contains image data of an MLO view and image data of a CC view, this is usually referred to as an ipsilateral recording.

When evaluating a tomosynthesis image data record, the diagnosing practitioner usually scrolls through the individual layers of the at least one tomosynthesis volume in the tomosynthesis image data record in order to be able to find lesions. The use of a so-called CINE mode, in which the various layers are automatically scrolled through from bottom to top to bottom at a specific frame rate, is also known. If lesions, e.g. microcalcifications or masses, are detected as target structures, these need to be analyzed and documented. The position at which the target structure is situated within the breast is also part of this documentation.

To this end, use is usually made of descriptors which describe the position of the target structure, in particular of a lesion, in a manner which is abstracted and suitable for the display in a pictogram, wherein e.g. it is suggested, in an article by Harmien Zonderland and Robin Smithuis, "Bi-RADS for Mammography and Ultrasound 2013", electronically retrievable from http://www.radiologyassistant.nl/en/p53b4082c92130/bi-rads-for-mammography-and-ultrasound-2013.html, to provide the following specifications during documentation:
1. Specification of the right or left breast,
2. Specification of a quadrant and a clock face notation in an abstracted frontal view,
3. A depth specification (e.g. anterior third, middle third or posterior third), and
4. Distance from the nipple (papilla mammae).

While it is usually conventional for the details of the documentation to be provided by the individual institutions, similar schemes do tend to be used in general, with the quadrant and clock face specifications being particularly common spatial descriptors.

A problem arising with the specification of such spatial descriptors is that these should relate to the non-compressed breast so that they can also be linked directly to all imaging results or can be taken into account in the case of an operative intervention. Consequently, such spatial descriptors require the diagnosing practitioner to estimate the look of the examined breast without the compression that was applied for the mammography recordings. Here, particular difficulties arise in tomosynthesis image data records since these represent the compressed breast in various layers. This increases the mental exertion required to undertake a correct localization of a specific lesion, and so there is a large time outlay and/or a high risk of errors.

Published, non-prosecuted German patent application DE 10 2010 063 810 A1, corresponding to U.S. patent publication No. 2012/0157819, discloses an imaging method and an imaging apparatus for displaying decompressed views of a tissue region. Here, the tissue region is introduced into the capture region of a first imaging modality, with the tissue region assuming a first form. After the interior of the tissue region was captured by means of the first imaging modality, a first image volume of the interior of the tissue region, when it assumes the first form, is ascertained. A first transformation of the first image volume into a second image volume, which represents the interior of the tissue when the tissue region assumes a second form, is displayed. The tissue region may be the mamma, the first imaging modality may be a digital breast tomosynthesis system, in which the breast of a patient is compressed between a compression plate and a compression table, and the second shape of the tissue region may be one in which no further pressure is exerted on the tissue or on the breast. The position of a marked first partial image volume may be indicated in the second image volume.

SUMMARY OF THE INVENTION

Therefore, the invention is based on the object of specifying an option for assisting the diagnosing practitioner when evaluating tomosynthesis image data records in respect of the position specifications of target structures, in particular lesions.

In this way, it is possible to automatically provide estimates of spatial descriptors or suitable pictograms for target structures to the diagnosing practitioner, which spatial descriptors or suitable pictograms were marked in terms of the position thereof in the three-dimensional tomosynthesis image data record, with the position of the target structure being described by the first spatial information item. The pictogram information item, which may already contain pictograms as abstracted, pictorial representations or at least facilitate the generation thereof, may in this case be output in real time on a user interface or provided as input data for a documentation system, for example radiology information system (RIS). Here, initially, a non-compressed breast shape is derived from the shape of the breast in the compressed state and mapping of positions, which are specified in the compressed breast shape, onto the non-compressed breast shape is thereupon facilitated, after which, in turn, mapping of the positions in the non-compressed breast shape onto a pictogram or any other abstracted, simplified representation is ascertained. The pictogram information item then emerges therefrom.

In so doing, it should already be noted here that the tomosynthesis image data record may, by all means, contain a plurality of views of the breast, for example image data from an MLO view and/or a CC view. Moreover, it is conceivable, as was already proposed in the prior art, for only the image data assigned to the MLO view to be included in the ascertainment of the second shape information item since the largest possible part of the breast tissue is captured in this case.

Consequently, a first shape information item is initially established in a first step, the shape information item describing the compressed shape of the breast as was present when recording the tomosynthesis image data record. If a plurality of views with different compressions are available, first shape information items are expediently established for all of these views. Ultimately, the first shape information item describes a geometric model of the breast which is ascertained from the reconstructed tomosynthesis images, i.e. the tomosynthesis image data record.

Here, it is preferable for the first shape information item to be ascertained on the basis of a segmentation of the breast surface and/or a detection of the nipple and/or the pectoral muscle. In particular, the nipple (papilla mammae) and the pectoral muscles (musculus pectoralis, abbreviated pecs) also constitute automatically detectable anatomical features which are suitable for describing the shape of the breast. Furthermore, it is very expedient for the breast surface to be determined by segmentation such that, ultimately, a surface mesh is provided. The prior art has already proposed various methods for ascertaining these partial information items of the first shape information item, which may also be employed within the scope of the present invention.

By way of example, an approach which uses the "Integrated Detection Network Tool Kit" (IDTK) may be used to detect the nipple; in this respect, cf. M. Sofka et al., "Integrated Detection Network (IDN) for pose and boundary estimation in medical images", in: IEEE Int. Symp. Biomed. Imag.: Nano to Macro, Chicago, Ill., USA, pages 294-299 (2011), which offers a framework for "Marginal Space Learning (MSL)", as described in the article by Y. Zheng et al. "Four-chamber heart modeling and automatic segmentation for 3D cardiac CT volumes using Marginal Space Learning and steerable features", in: IEEE Trans. Med. Imag. 27(11), pages 1668-1681 (2008). Here, use may be made of a bootstrap position detector which uses hair-like features. This embodiment would be an example of a learning system which is trained during a learning phase. Naturally, a multiplicity of other options which permit detection and consequently localization of the nipple, in particular by image processing methods, are also conceivable.

The prior art has also already disclosed a multiplicity of methods for detecting the pectoral muscles, with use preferably being made in the present case of the method described in published, European patent application EP 2 693 400 A2 for the automatic detection of a pectoral muscle. In respect of ascertaining a breast surface from a tomosynthesis image data record, reference is made to the method in EP 2 634 748 A1, corresponding to U.S. Pat. No. 9,235,888, which is herewith incorporated in its entirety in the disclosure of the present invention by reference.

Thereupon, the breast shape in a non-compressed state is estimated in a second step of the method according to the invention. To this end, the use of a data-driven determination method and/or a determination method based on a biomechanical simulation may be provided to ascertain the second shape information item. A particularly preferred method is described in the already mentioned EP 2 634 748 A2, wherein a data-driven regression method is ultimately used for a predictive determination of a set of target shape parameters of a target shape model, which regression model was derived from existing radiological image data (training image data). The second shape therein, in the current specific application the non-compressed breast shape, is consequently described as second shape information item by the target shape parameters determined in the regression method.

While the approach of EP 2 634 748 82, which ultimately targets the representation of the tomosynthesis image data in another form, makes do without explicit biomechanical parameters, approaches which use biomechanical simulations, that is to say e.g. attempt to analyze the behavior when the compression plate ("paddle") is removed, are also conceivable for application in the method according to the invention. However, these are less preferable in the context of ascertaining the second shape information item in the method according to the invention; however, as is intended still to be explained in more detail below, the approach of a biomechanical simulation is extremely expedient when ascertaining the second spatial information item.

This is now carried out in a third step of the method according to the invention, wherein it is particularly preferable for ascertaining the second spatial information if a biomechanical simulation of the movement of at least the position described by the first spatial information item from the compressed breast shape to the non-compressed breast shape is carried out and/or if a thin plate spline transformation (TPS transformation) is carried out on the basis of reference positions which are localizable in both breast shapes. Consequently, a combination of a data-driven approach (for determining the second shape information item) and an approach based on a biomechanical simulation (for ascertaining the second spatial information item) is conceivable in particular. Biomechanical parameters are then used to observe the behavior of tissue points not described in the shape information transitioning from the compressed breast shape to the non-compressed breast shape and correspondingly be able to determine how the position described by the first spatial information item also changes.

However, it is particularly advantageous if a TPS transformation is used; incidentally, as is also described in the already mentioned EP 2 634 748 A1. From a computational point of view, the use of TPS transformations is very efficient and it may thus easily be used in real-time applications. Here, the use of the TPS models may be based on the aforementioned determination of the breast surface and the detection of the nipple and the pectoral muscles as provision may be made for a geometric curve to be determined in such a way that the curve, at least approximately, extends along the breast surface and through a plurality of anatomical landmarks. This determination of the geometric curve occurs both in the compressed breast shape and in the non-compressed breast shape. Subsequently, curve points are determined in the geometric curves, with, preferably, curve points being distributed uniformly between pairs of anatomical landmarks, that is to say, for example, arranged equidistantly. Thereupon, a plurality of contours are determined on the breast surfaces of the compressed and non-compressed breast shape, with the determination of the contours being selected in such a way that respectively one contour runs through one curve point. Preferably the contours are so-called splines. Within the mathematical sense, a spline is a curve which extends through a specific number of points and connects these "smoothly" to one another. The geometric position of the target structure in the non-compressed breast shape is described depending on the contours in the non-compressed breast shape by means of an interpolation, preferably by a TPS interpolation as mentioned above, between the contour points of the compressed shape and the non-compressed breast shape. Here, thin plate splines are advantageously used in order to describe the deformation of the volume when converting from the compressed to the non-compressed shape on the basis of the aforementioned anatomical breast surfaces.

After this third step is completed, the position of the target structure is now known in any case in the non-compressed breast shape, described by the second spatial information item.

As already described above, the tomosynthesis image data record may comprise a plurality of views, for example an MLO view and a CC view, in which there are different compressions of the breast and/or different views of the same compression are provided. Consequently, different second spatial information items may result from the different views, in particular in the case of different compressions, and these should be referred to as preliminary information items below. This should not be assessed as disadvantageous but may, instead, lead to a more accurate, more reliable determination of the second spatial information item.

Thus, in the case of a plurality of views of the breast contained in the tomosynthesis image data record, the present invention provides for a second preliminary spatial information item to be ascertained for each view, to which view, in particular, a compressed breast shape is assigned in each case, wherein the second spatial information to be used further is ascertained by statistical combination of the preliminary spatial information items. Thus, if, in particular, the mapping of the position described by the first spatial information item in the compressed breast shape onto the position in the non-compressed breast shape described by the second spatial information item is carried out independently for the various views, different positions may result, with obtaining a single, common second spatial information item (and hence also pictogram information item) for the target structure naturally being desired. Consequently, in order to obtain consistent pictogram information items, the statistical combination of the preliminary spatial information items is proposed. Although, in principle, it is conceivable here to ascertain the second spatial information item by forming the mean value from the preliminary spatial information items, provision is however made according to the invention for the mean value formation to be weighted by a reliability value, in particular a directionally resolved reliability value, which is assigned to the respective preliminary information item.

First, such reliability values may often take account of already supplied reliability variables/error values by algorithms which calculate mappings, for example the aforementioned TPS algorithms.

However, it is preferable for such reliability values to depend on the type of compression of the mamma in the compressed breast shape (and optionally on the view) because it was found that the first spatial information items may be determined more exactly in certain directions (in which no compression is present) than in other directions (in which a compression is present). However, if a different compression of the breast is provided for the different views, and different compressed breast shapes are consequently present, as is e.g. the case for the MLO view in comparison with the CC view, the most exact spatial information items in both views are provided in different directions. Consequently, if the components of the directions in which the spatial information item may be determined more exactly in the given compression are introduced with a stronger weighting into the formation of the average in each case, this results in a significantly improved and more exact determination of the second spatial information item after the anisotropic uncertainty of the preliminary spatial information when calculating the final second spatial information item is taken into account and if the fact that a plurality of measurements having different spatial resolution characteristics are available is employed. Consequently, the procedure described thus permits not only the mapping of positions described by the first spatial information item onto a consistent pictogram information item but also an improvement in the determination of same by complementing the accuracies.

In the step of the method according to the invention following next, the second spatial information item is then transformed into the pictogram information item. To this end, substantially two approaches are conceivable; naturally, both may also be used. First, there may be a transformation of the position described by the second spatial information item in the non-compressed breast shape onto a fixed, predefined pictogram shape; second, it is however also possible to use general 3D rendering methods to be able to form a patient-specific pictogram. Here, the first possibility is advantageous in that it is possible to achieve standardization and the diagnosing practitioner may continue to work with descriptors and pictograms already known to him. The advantage of the variant specified second is that a more patient-adaptive and therefore more realistic geometric visualization of the position of target structures is facilitated.

In accordance with the first, preferred approach, provision may be made for the transformation of the second spatial information item into the pictogram information item to comprise the mapping of the position described by the second spatial information item in the non-compressed breast shape into a pictogram model describing a pictogram breast shape. Various options are also conceivable in this context of "mapping" onto a predetermined pictogram breast shape.

Thus, by way of example, provision may be made for a predetermined mapping prescription, which is defined for all breast shapes covered by the breast model, to be used when ascertaining the second shape information item on the basis of a regression in a statistical breast model covering possible breast shapes. Consequently, if, for example, the procedure known from published, European patent application EP 2 634 748 A1 were to be used, the latter uses a statistical model of breasts obtained from training data, in particular keyed according to sex, which consequently covers the anatomically conceivable, and therefore possible, breast shapes overall. In other words, the statistical model of the breast is configured in such a way that it may describe, where possible, all non-compressed breast shapes possible in reality, for the purposes of which it is preferably based on a principal component analysis (PCA). However, if the breast shapes covered by the statistical model are pre-known overall in a mathematically describable manner in advance, this a priori knowledge may be used likewise to define a generic imaging prescription a priori.

In this context, it is particularly advantageous if point correspondences between projections, which are established from the projected covered breast shapes and correspond to the abstracted view of the pictogram, and at least one pictogram, which is to be used and derivable from the pictogram model, are used to define the mapping prescription. In other words, it is possible to define point correspondences between a suitable projection of the three-dimensional statistical model and the pictogram (or the pictograms), wherein positions may once again be mapped onto the pictogram using TPS transformations.

Alternatively, it is also conceivable for a coordinate system, in particular a cylindrical coordinate system, used to describe positions in the pictogram model to be registered with the non-compressed breast shape described by the second shape information item for the purposes of facilitating the mapping into the pictogram model. Here, this may preferably be a cylindrical coordinate system which, for example, is suitable if one of the at least one pictograms relates to a circular, stylized front view of the breast, in which a position may e.g. be specified as a quadrant specification and/or in a clock face notation. Then, preferably, a further pictogram relates to depth sectors, for example the anterior third, the middle third and the posterior third of the breast, imaged by way of the longitudinal axis of the cylinder. Such a coordinate system, in particular a cylindrical coordinate system, may be characterized by at least one labeled point which may be established on the basis of the second shape information item and/or by at least one direction which may be established on the basis of the second shape information item. In a specific example, this means that the nipple may be used as a labeled point known in the respective shape information items while the posterior-anterior direction, preferably likewise known in the shape information item, is used as direction to define a cylindrical coordinate system. In other words, the axis of rotation of a cylindrical coordinate system may be defined through the nipple and in a direction toward the pectoral muscles. As already explained, it is then possible to realize front view pictograms, preferably quadrant- or clock-face-based front view pictograms, and side view pictograms relating to depth ranges in such a cylindrical coordinate system. In order to facilitate the transformation of the second spatial information item into this cylindrical coordinate system of the pictogram model, use is expediently made of a registration process as, in principle, is already known. At this point, it should further be noted that the nipple need not necessarily form the relevant point for defining the cylindrical coordinate system; instead, it is by all means conceivable to use other labeled points, for example a center of mass or the like.

In a configuration of the present invention supplying patient-specific pictograms instead, it is possible, as already indicated, for provision expediently to be made for the transformation of the second spatial information item into the pictogram information item to comprise at least one rendering process in respect of the non-compressed breast shape described by the second shape information item. What is employed here is that it is possible to use generic 3D rendering methods for generating pictogram-like or schematic views of the breast since an estimate of the shape of the breast and the positions of the target structures in the three-dimensional space of the non-compressed breast are known. This is advantageous in that a patient-specific pictogram is generated, which better reproduces the true geometry of the examined breast. Here, various rendering approaches are conceivable.

Thus, provision may be made e.g. for the surface of the non-compressed breast shape determinable from the second shape information item and the position of the target structure described by the second spatial information item to be used as data record to be rendered. Consequently, there may be biometric rendering of the mesh model of the breast surface together with the position of the target structure in the non-compressed breast. Here, the breast surface may, at least in part, be displayed transparently, for example as a mesh.

Another approach provides for a volume data record, distinguishing in particular in binary fashion between regions belonging to the non-compressed breast shape and regions not belonging to the non-compressed breast shape, with the position of the target structure which is marked therein and described by the second spatial information item to be used as data record to be rendered. Thus, an artificial voxel volume is generated in this case from the geometric model of the non-compressed breast, as described by the second shape information item, together with the position to be displayed, and this is rendered using a generic volume rendering algorithm. It should be noted that such a volume data record to be rendered may also be used for generating MPR-like images or projection images (by a forward projection in the volume data record) as pictograms, in which the position of the corresponding target structure may then be identified. If the assumption of a binary display is in fact made here, positions of target structures may be displayed very intuitively, for example by means of three orthogonal, selected MPR-like pictograms in orthogonal layers containing the position.

What is particularly advantageous in all these approaches based on rendering is if there is a dynamic adaptation of the pictogram information item, in particular the depicted pictogram information item, depending on at least one user input, describing a modified rendering parameter, for rotating and/or for zooming and/or for displacing the pictogram obtained by the rendering process. Consequently, an interactive 3D visualization of the pictograms is conceivable, the 3D visualization permitting rotating, zooming and displacing of the view such that the spatial understanding of the observer in relation to the position of the target structure within the non-compressed breast may be significantly improved. Naturally, it is also conceivable to use predefined views when rendering.

As already mentioned, the pictogram information item need not necessarily consist of the pictogram itself, but may also contain the descriptors required for generating the pictogram. Thus, provision may also be made for spatial descriptors facilitating the display of the position of the target structure in at least one pictogram to be established as pictogram information item. Here, it is particularly preferable if the descriptors comprise a quadrant, in which the target structure is situated, and/or a directional specification of the target structure in the pictogram, related to clock face notation, and/or a depth information item in the anterior-posterior direction, in particular in relation to depth sectors depicted in a distinguishable manner in the pictogram, and/or a distance to a labeled point or a labeled surface which is also depicted in the pictogram. By way of example, it is conceivable to derive quadrants and clock face notations of a target structure, in particular a lesion, from the mapping to a cylindrical coordinate system, as already described above. An associated distance to a nipple in particular defining the longitudinal axis of the cylindrical coordinate system may likewise be established in this projection space on the basis of the mapping.

Stated in general terms, distances from a reference point or a reference surface, in particular from the nipple, the pectoral muscles and the breast surface (skin line), may be determined in the recorded compressed breast just like in the non-compressed breast since the complete geometry of the breast in these spaces is known on the basis of the first shape information item and the second shape information item. An advantage of measuring the distances in the non-compressed breast shape is that a single, consistent measure is obtained for different views, in particular since the second spatial information item may preferably be obtained in a manner improving the quality of the second spatial information item by combining preliminary spatial information items of different views, as described above.

In order to establish spatial descriptors relating to the depth, for example the positions in an anterior, middle or posterior third, the geometric model of the non-compressed breast emerging from the second shape information item may be subdivided into corresponding depth sectors such that to which depth sector the target structure should be assigned may easily be established on the basis of the second spatial information item.

Thus, in conclusion, the method according to the invention allows automatic derivation of pictograms or spatial descriptors facilitating the creation of pictograms by virtue of use being made of a virtually non-compressed model of the breast such that the susceptibility of the documentation process to errors is reduced and the accuracy is increased.

In addition to the method, the present invention also relates to an apparatus for assisting a diagnosing practitioner with describing the location of at least one target structure in a tomosynthesis image data record of a compressed breast of a patient, the target structure being localized by means of a first spatial information item, the apparatus containing a receiving interface for receiving the tomosynthesis data record, a computer device for carrying out the method according to the invention and an output interface for outputting the pictogram information item and/or a representation derived therefrom. Here, the output interface may be directed to an output medium, for example a user interface, but it is also conceivable to forward the pictogram information directly to a system that is used for documentation, for example a radiology information system (RIS). The interfaces mentioned here may be realized as software and/or hardware; the computer device may also comprise software and/or hardware components, for example a processor and a memory device. All embodiments in respect of the method according to the invention may be transferred in an analogous manner to the apparatus according to the invention, and so the latter may also obtain the advantages already specified above.

In particular, the computer device of the assistance apparatus according to the invention consequently realizes the following:

a) an ascertainment unit for ascertaining a first shape information item describing at least one first, compressed breast shape in the tomosynthesis image data record, b) a determination unit for determining a second shape information item describing the breast in a non-compressed breast shape from the first shape information item, c) a transfer unit for mapping the position of the at least one target structure from the compressed breast shape and to the non-compressed breast shape using at least the second shape information item for ascertaining a second spatial information item relating to the non-compressed breast shape, and d) a transformation unit for transforming the second spatial information item into a pictogram information item facilitating an abstracted pictorial representation and/or describing the latter. Naturally, it is also conceivable to provide functional units which realize further advantageous steps discussed in respect of the method according to the invention or to further characterize the functional units specified here by appropriate subunits.

Finally, the invention also relates to a computer program which carries out the steps of a method according to the invention when it is run on a computer device. For the computer program too, the explanations made in respect of the method and the apparatus continue to apply. The computer program may be available on an electronically readable, non-transient data medium, for example a CD-ROM.

Other features which are considered as characteristic for the invention are set forth in the appended claims.

Although the invention is illustrated and described herein as embodied in a method for assisting a diagnosing practitioner with describing the location of a target structure in a breast, apparatus and a computer program, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
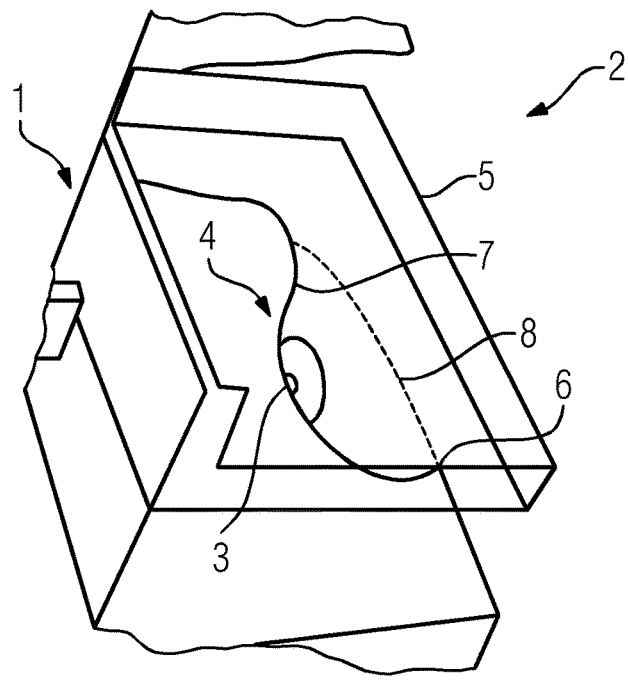
FIG. 1 is a diagrammatic, perspective view of a recording device for imaging a breast according to the invention.

Referring now to the figures of the drawings in detail and first, particularly to FIG. 1 thereof, there is shown schematically part of a mammography device 1, by which tomosynthesis image data records of a breast 4 of a patient 2 may be recorded. In particular, the mammography device 1 depicted in sections may be used to generate DBT image data as tomosynthesis image data record. Here, the breast 4 is affixed and compressed by a mechanical mechanism, the so-called paddle 5, with FIG. 1 showing a positioning of the patient 2 in the MLO position for recording tomosynthesis image data in an MLO view. The nipple 3 (papilla), the top of the breast 7 and the inframammary crease 6, which is also referred to as inframammary fold in medical practice, are also depicted. Moreover, the edge of the pectoral muscle 8, which may be considered to be the line or area delimiting the breast 4 from the remainder of the body of the patient 2, is indicated using a dashed line.

Figure 2:
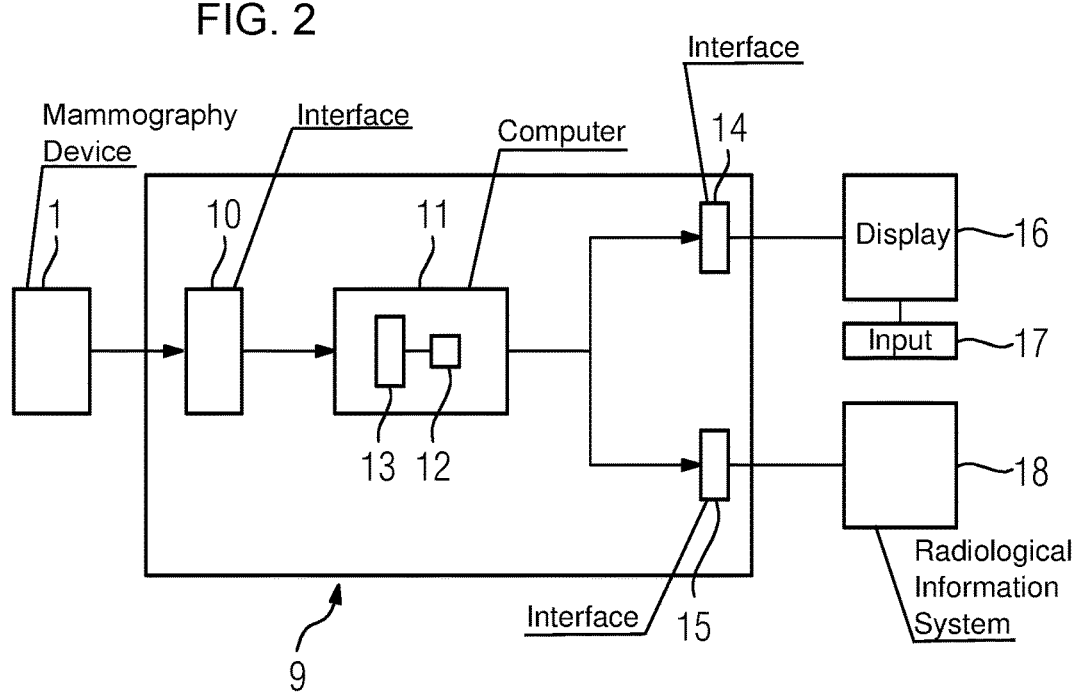
FIG. 2 is a block diagram showing an assistance apparatus according to the invention.

FIG. 2 shows an apparatus 9 according to the invention for assisting a diagnosing practitioner with describing the location of at least one target structure localized in a tomosynthesis image data record of a compressed breast 4, with the position of the target structure localized in the tomosynthesis image data record being described by a first spatial information item. The assistance apparatus 9 contains a receiving interface 10 for receiving a tomosynthesis image data record and the first spatial information item. These data may be transmitted directly by the mammography device 1, or else by way of an intermediate apparatus, for example a diagnosing workstation, at which target structures, for example lesions as target structures, were marked in terms of the position thereof.

A computer device 11, which in the present case contains at least one processor 12 and a memory device 13 connected therewith, is embodied to carry out the method according to the invention, as is yet to be explained in more detail below. Thus, from the first spatial information and in the tomosynthesis image data record, the computer device 11 determines a pictogram information item, which either already contains a pictogram or else may be used to generate such an abstracted pictorial representation. The pictogram information item is output by way of at least one of two output interfaces 14, 15, with the output interface 14 in the present case being assigned to a display apparatus 16, where the pictogram may be observed, for example within a corresponding user interface. An input apparatus 17, by means of which, for example, parameters for generating the representation from the pictogram information item, or even for generating the pictogram information item itself, may be adapted, is assigned to the display apparatus 16. The pictogram information item and the corresponding pictograms may, in the present case, be generated in real time, and consequently rendering parameters may be adapted e.g. in the case of pictograms which arose by rendering, which rendering parameters may be used for rotating the pictogram, zooming and/or for displacing the point of view.

The output interface 15 is assigned to a radiology information system 18 (RIS), in which the pictogram information item may be stored for documentation purposes, for example in order, at a later stage, to facilitate a comparison with image data from a different modality and/or plan an intervention.

Figure 3:
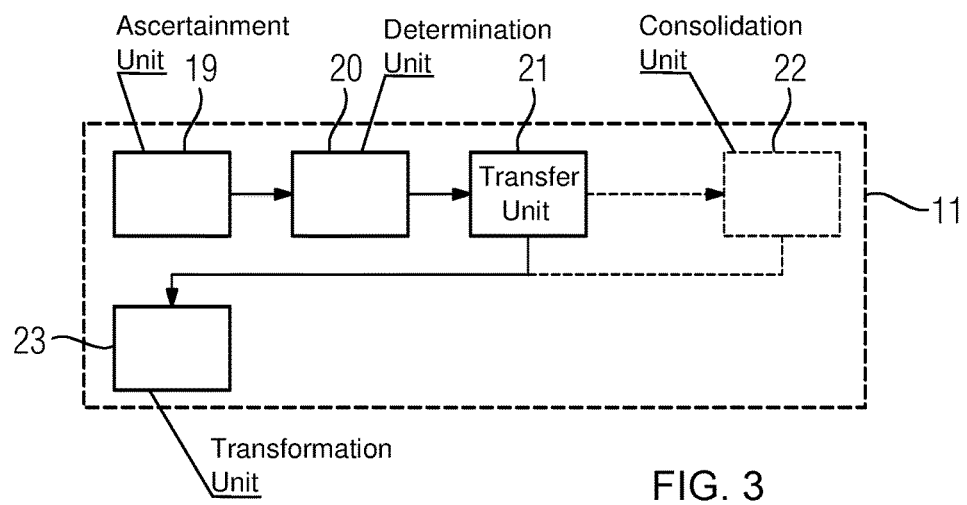
FIG. 3 is a block diagram showing functional units of a computer device in the assistance apparatus of FIG. 2.

FIG. 3 shows the functional design of the computer device 11 in more detail. It initially contains an ascertainment unit 19, which is embodied to ascertain a first shape information item describing at least one first, compressed breast shape in the tomosynthesis image data record, corresponding to carrying out a first step of the method according to the invention. Consequently, the first shape information item describes the compressed breast shape while image data of the tomosynthesis image data record are recorded, with a dedicated first shape information item being established in the present case for each type of compression, for example the different compressed breast shape in an MLO view and CC view. Thus, ultimately, the first shape information item describes a geometric model of the compressed breast 4. The first shape information item contains the breast surface of the compressed breast 4, which has a mesh description in the present case. The breast surface is determined by a known segmentation method which evaluates the tomosynthesis image data of the corresponding view in the tomosynthesis image data record, i.e., in particular, the reconstructed, three-dimensional tomosynthesis images. Furthermore, the pectoral muscles 8, at least in the form of the line delimiting the breast 4, and the nipple 3 are detected and hence localized by evaluating the image data of the tomosynthesis image data record, which is likewise included in the first shape information item. Here too, as a matter of principle, it is possible to use known image processing algorithms; by way of example, the method described in published, European patent application EP 2 693 400 A2 may be used to detect the pectoral muscles. In the present case, the procedure described in published, European patent application EP 2 634 748 A1 is used to determine the breast surface in a surface mesh model.

A determination unit 20 is provided for carrying out a second method step; consequently, it is embodied to determine a second shape information item describing the breast in a non-compressed breast shape from the first shape information item. Here too, use is made in the present case of the procedure described in published, European patent application EP 2 634 748 A1, which is ultimately based on a statistical model which covers all anatomically possible breast shapes and uses a regression to be able to find the model instance of the statistical model describing the non-compressed breast shape assigned to the compressed breast 4. Here too, biomechanical simulations may be taken into account in different exemplary embodiments. Reference is made to the fact that, on account of the nature of the procedure, which orients itself on the breast surface, the delimitation of the breast 4 by the pectoral muscles 8 and the position of the nipple 3, the breast surface and the two anatomical features are also known by the second shape information item.

In a transfer unit 21, which is assigned to a third step of the method, it is now possible to map the position of the at least one target structure, in particular a lesion, described by the first spatial information item, from the compressed breast shape, described by the first shape information item, to the non-compressed breast shape, described by the second shape information item, in order to ascertain a second spatial information item related to the non-compressed breast shape. Consequently, "mapping" takes place, in which positions related to target structures, in particular lesions, are transferred from the compressed breast shape to the non-compressed breast shape. To this end, in the present case thin plate spline transformations (TPS transformations) are used in a computationally very efficient manner, and consequently permitting real-time applications, as described in more detail by published, European patent application EP 2 634 748 A1. Here too, it is possible to alternatively or additionally resort in other exemplary embodiments to biomechanical simulations of the interior of the breast 4.

The consolidation unit 22 is optional, and hence also assigned to an optional fourth step of the method. In the present case, it is used since tomosynthesis image data (DBT data) are present both in the MLO view and in the CC view in the tomosynthesis data record considered in an exemplary fashion. The corresponding tomosynthesis image data are recorded in different compressed breast shapes. The medical practitioner has now marked the target structure, for example a lesion, or used diagnosis software to find it automatically, in the two resulting three-dimensional tomosynthesis images, and so first spatial information items describing positions are available for both views. These need not necessarily have the same second spatial information item as a consequence, although this is desired in view of consistency.

Consequently, second spatial information items as preliminary information items were determined in the transfer unit 21 for both the MLO view and the CC view in the third step. These are now statistically combined in the consolidation unit 22, with a weighted mean value being formed in the present case in order to ascertain the final, second spatial information item to be used further. Here, an anisotropic reliability value is used for weighting; it is used in such a way that the overall quality of the second spatial information item is even improved when the accuracy of determining the first spatial information item is taken into account. This is because, in the different views, determining the position when ascertaining the first position information item is more exact in different directions on account of the different compressions and views; this is expressed by the reliability value, which may e.g. be assigned to specific directions. Furthermore, reliability information items supplied by the algorithms used by the units 19 to 21 may also be included in the reliability value. After weighting has been carried out using the (anisotropic) reliability value, the more precisely determined portions of the individual preliminary spatial information items have a greater influence, significantly improving the overall accuracy of determining the second spatial information item. The fourth step described here, or the consolidation unit 22, are used in this case since different views are in fact present in the tomosynthesis image data record.

Once the second spatial information item is ascertained, it is forwarded to a transformation unit 23, which is assigned to a fifth step of the method and which is embodied to transform the second spatial information item into a pictogram information item facilitating an abstracted pictorial representation and/or describing the latter.

Here, there are two different options, which both have advantages and which may also both be used in parallel. Thus, firstly, positions of the non-compressed breast shape may be mapped to a predefined pictogram shape, for example described by a pictogram model; however, it is also possible for general 3D rendering methods to be used in order to obtain a patient-specific pictogram. Here, reference is once again made to the fact that it is not necessarily the pictogram itself which needs to be ascertained and output as pictogram information item; rather, it is by all means possible that spatial descriptors, from which the pictogram may easily be constructed, i.e., for example, attributes of a point to be plotted in a predetermined pictogram shape, may be established as well. This will still be discussed in more detail in the discussion of specific pictograms.

What is employed here in the first case, and consequently when using a predetermined pictogram shape described by a predetermined pictogram model, is that the space of non-compressed breast shapes is known from the employed statistical model, see also published, European patent application EP 2 634 748 A1. This was employed by virtue of a mapping prescription being defined which may be employed for all breast shapes covered by the statistical breast model. Since the breast in the present case is assumed to be substantially cylindrical in the pictogram model such that an abstracted front view may be generated as a first pictogram and a side view describing depth regions may be generated as a second pictogram, it is possible, for example, to generate corresponding projections of the non-compressed breast shapes, and consequently possible to generate frontal and lateral views. Point correspondences to the respective pictograms are set for these, from which the mapping prescription emerges.

As an alternative to such a procedure, it is also possible in another exemplary embodiment for a coordinate system, which is used to describe positions in the pictogram model and which is cylindrical in the presently used pictogram model, to be registered to the non-compressed breast shape described by the second shape information item for the purposes of facilitating the mapping into the pictogram model. In so doing, a cylindrical coordinate system is expediently used in the present case, the axis of rotation of which being defined by the nipple 3 and a direction toward the pectoral muscle 8. As described above, these information items may easily be derived from the second shape information item. Hence, a mapping prescription exists from the non-compressed breast shape into the cylindrical coordinate system which permits the transformation of the second spatial information item to the pictogram information item.

If use should also be made of patient-specific pictograms which reflect the specific breast shape, there is a definition of data records to be rendered, for example by the breast surface together with the position described by the second spatial information item, or else as volume data record in which, in particular, there is a binary distinction made between regions belonging to the breast 4 and regions not belonging to the breast 4. In such a volume data record too, the voxel in which the position of the second spatial information item lies is naturally marked appropriately. Precisely these approaches which use a rendering process lend themselves to interactive 3D visualizations, as was described in respect of the input device 17.

FIG. 4 once again briefly summarizes the described method for assisting the diagnosing practitioner with describing a location for documentation purposes, and also already shows an example of a pictogram 24, which is based on a cylindrical coordinate system and, consequently, a cylindrical pictogram model facilitating, in an abstracted manner, a front view of the breast 4.

The described method therefore proceeds from a tomosynthesis image data record, with a reconstructed tomosynthesis image 25 of an MLO view being shown schematically as initial point, and a target structure 26, in this case lesion, which is marked in the tomosynthesis image 25 and the position 27 of which is described by the first spatial information item. By means of steps one through four of the method, this position 27, symbolized by the arrow 28, is transferred to a position 29 in a non-compressed breast shape 30 of the breast 4.

The last, fifth step of the method, which is symbolized by the arrow 51, now transfers the second spatial information item into the pictogram model (and additionally, or alternatively, a rendered pictogram) such that a position 31 may be displayed in a pictogram 24, for the purposes of which the correspondingly ascertained pictogram information item is used.

Figure 4:
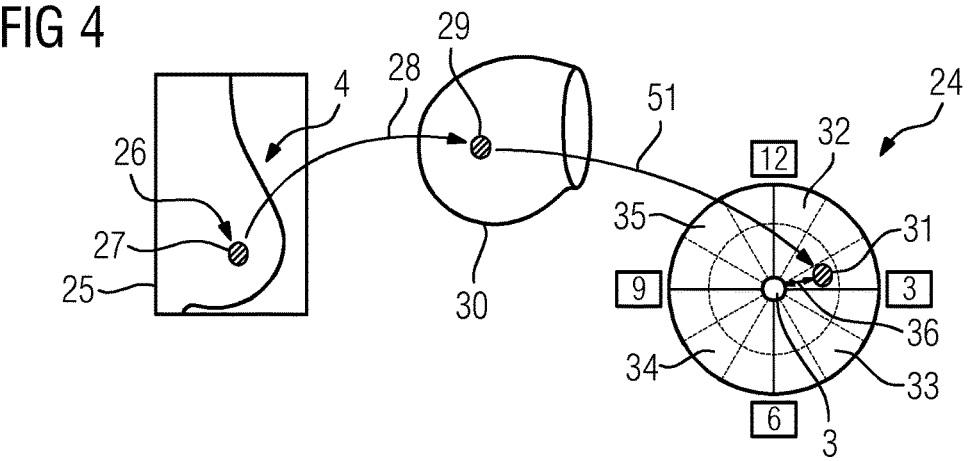
FIG. 4 is a sketch for explaining a method according to the invention.

The pictogram 24 depicted in FIG. 4 substantially corresponds to an abstracted front view of the breast 4, the center of which is also formed by the nipple 3 defining the axis of rotation of the cylindrical coordinate system, facilitating intuitive orientation. It is clear that the breast 4 approximated by a circle in the pictogram model is not only subdivided into four quadrants 32 to 35, but also complemented by a clock face representation, in which the first quadrant 32 corresponds to hand positions from 12 to 3 o'clock, the second quadrant 33 corresponds to hand positions from 3 to 6 o'clock, the third quadrant 34 corresponds to hand positions from 6 to 9 o'clock and the fourth quadrant 35 corresponds to hand positions from 9 to 12 o'clock. In the present case, the position 31, which may be described by a corresponding spatial descriptor in the pictogram information item, lies at approximately 2:30, with a further spatial descriptor of the pictogram information item relating to the distance of the target structure from the nipple 3, which is likewise visualized, cf. the double-headed arrow 36, in the pictogram 24.

Figure 5:
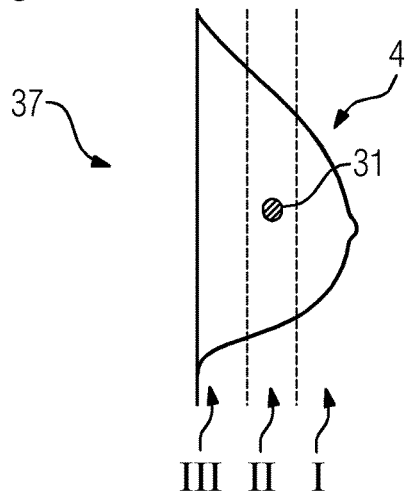
FIG. 5 is a pictogram indicating depth sectors.

The pictogram 24 also includes the abstracted lateral display of the breast 4 as pictogram 37 in FIG. 5, in which the breast is subdivided into depth sectors I, II and III in the anterior-posterior direction, wherein the depth sector I comprises the anterior third of the breast 4, the depth sector II contains the middle third of the breast 4 and the depth sector III contains the posterior third of the breast 4. Now, at least belonging to one of the depth sectors I to III is part of the pictogram information item, with it naturally also being possible for a more exact depth specification to be present, the latter facilitating the position 31 also to be depicted in the pictogram 34.

In the present case, the pictogram information item may consequently, when using the pictograms 24, 37, comprise a clock face directional specification, a distance from the nipple 3 and a depth information item, in particular belonging to a depth sector I to III as descriptors, wherein, naturally, further information items may be present in a supplementary manner or, in other exemplary embodiments, different pictograms with other underlying pictogram models may be used.

Figure 6:
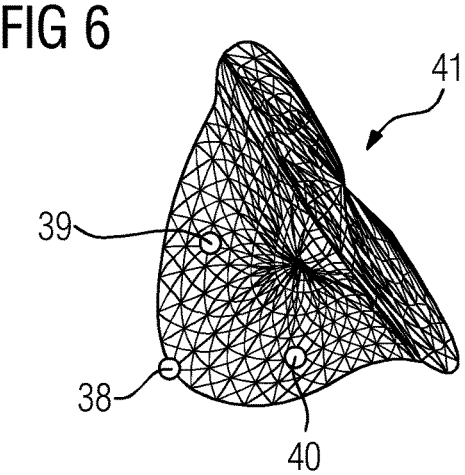
FIG. 6 is a pictogram ascertained by rendering in a first view.
Figure 7:
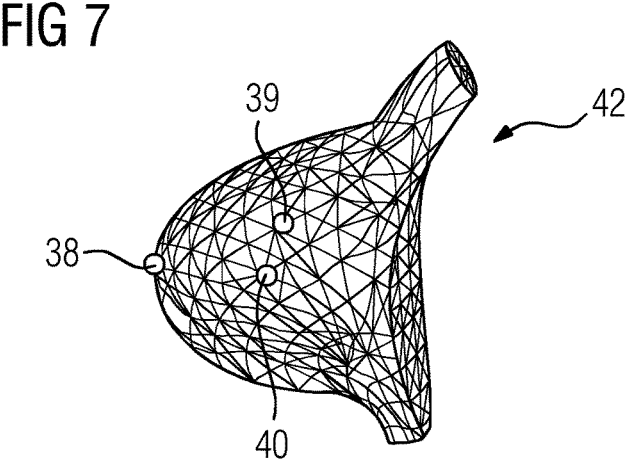
FIG. 7 is a pictogram ascertained by rendering in a second view.
Figure 8:
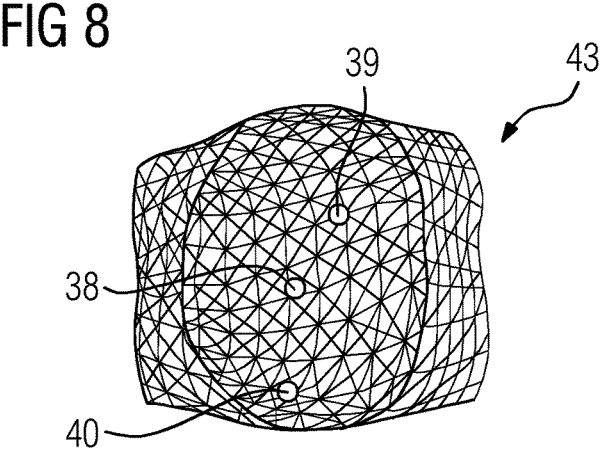
FIG. 8 is a pictogram ascertained by rendering in a third view.

As mentioned previously, it is also possible to generate patient-specific pictograms, and consequently pictograms reproducing the specific non-compressed breast shape 30, by way of rendering, with FIGS. 6 to 8 showing various rendered views of the non-compressed breast shape 30 with position markers 38, 39 and 40 as pictograms 41, 42 and 43 shown therein. Here, the position marker 38 indicates the position of the nipple 3 and the position markers 39 and 40 indicate the positions of target structures, for example lesions. The pictogram 41 corresponds to an MLO view, the pictogram 42 corresponds to a CC view and the pictogram 43 corresponds to a dorsal view.

The pictograms emerged from rendering a data record which contains the breast surface in the non-compressed breast shape 30, the position of the nipple 38 and the positions of the target structures described by the corresponding second spatial information items.

Figure 9:
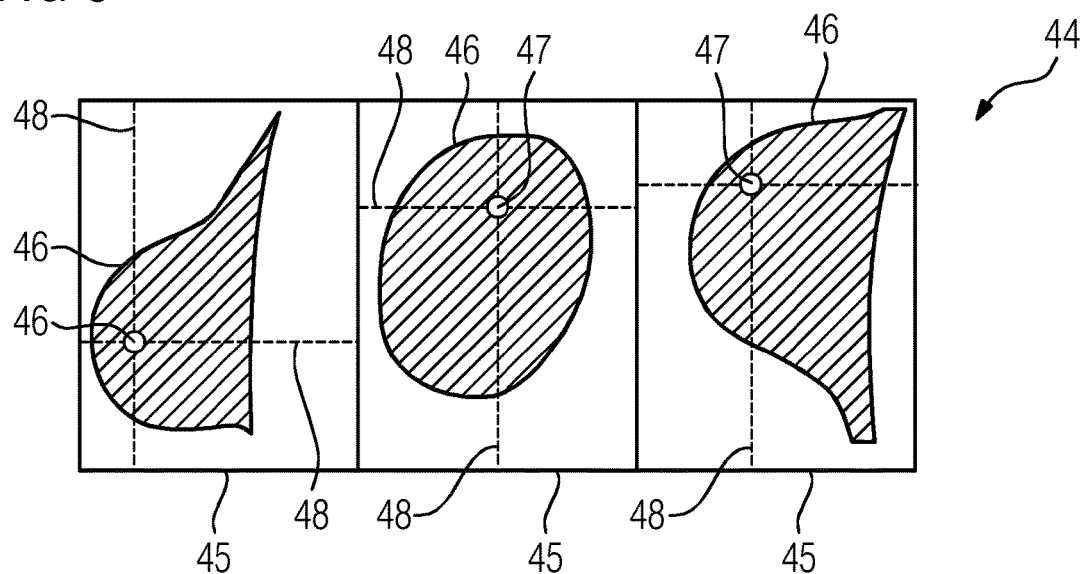
FIG. 9 is an illustration showing three mutually orthogonal, MPR-like pictograms.

Alternatively, it is also possible to generate a volume data record, in particular binary volume data record, which is subdivided into regions which belong to the breast 4 and regions which do not belong to the breast 4. Additionally, voxels corresponding to the position 29 of the target structure 26 are marked accordingly. This facilitates not only volume-rendered representations, but also MPR-like representations as pictograms, as explained in more detail by FIG. 9. The pictogram 44 depicted therein contains three mutually orthogonal MPR representations 45, which each contain regions 46 clearly belonging to the breast 4 and the position markers 47 for the voxel marked correspondingly for the target structure. For improved orientation, the lines 48 moreover indicate the positions of the respective other MPR layers. Naturally, the MPR layers underlying the MPR representations 44 were selected in such a way that the voxel marked for the target structure 26 lies therein.

Figure 10:
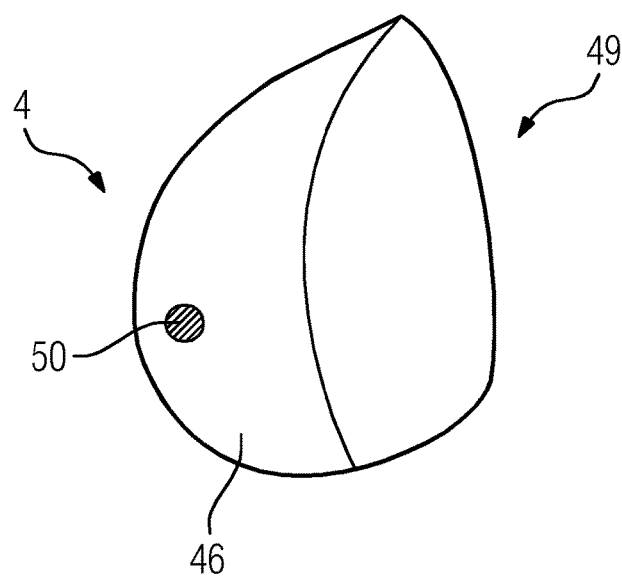
FIG. 10 is a pictogram rendered from a volume data record.

Finally, FIG. 10 shows as a further pictogram 49 a representation of the breast 4 obtained by a conventional volume rendering process from the described volume data record, in which representation regions 46 belonging to the breast 4 were set to be transparent such that the marked voxel as position marker 50 is also clearly identifiable in the pictogram 49. Here too, a real-time 3D visualization accessible to the change of rendering parameters by means of the input apparatus 17 may be expedient.

The invention claimed is:

1. A method for assisting a diagnosing practitioner with describing a location of at least one target structure in a tomosynthesis image data record of a compressed breast of a patient, the target structure being localized by means of a first spatial information item, which comprises the steps of:
   ascertaining a first shape information item describing at least one first compressed breast shape in the tomosynthesis image data record;
   determining a second shape information item describing the compressed breast in a non-compressed breast shape, from the first shape information item;
   mapping a position of the at least one target structure from the first compressed breast shape and to the non-compressed breast shape using at least the second shape information item for ascertaining a second spatial information item relating to the non-compressed breast shape; and
   transforming the second spatial information item into a pictogram information item facilitating an abstracted pictorial representation and/or describing the abstracted pictorial representation, wherein, in a case of a plurality of views of the compressed breast contained in the tomosynthesis image data record, a second spatial information item is ascertained for each view, the second spatial information item to be used is ascertained by statistical combination of preliminary spatial information items, with the second spatial information item being ascertained by forming a mean value, weighted by a reliability value assigned to a respective preliminary spatial information item, from the preliminary spatial information items.

2. The method according to claim 1, which further comprises ascertaining the first shape information item on a basis of a segmentation of at least one of a breast surface, a detection of a nipple or a detection of a pectoral muscle.

3. The method according to claim 1, which further comprises using at least one of a data-driven determination method or a determination method based on a biomechanical simulation for ascertaining the second shape information item.

4. The method according to claim 1, wherein in order to ascertain the second spatial information item, carrying out at least one of a biomechanical simulation of a movement of at least a position, described by the first spatial information item, from the compressed breast shape to the non-compressed breast shape or a thin plate spline transformation on a basis of reference positions which are localizable in both the compressed and non-compressed breast shapes.

5. The method according to claim 1, wherein a transformation of the second spatial information item to the pictogram information item includes mapping of a position, described by the second spatial information item, in the non-compressed breast shape into a pictogram model describing a pictogram breast shape.

6. The method according to claim 5, wherein when ascertaining the second shape information item on a basis of a regression in a statistical breast model covering possible breast shapes, use is made of a predetermined mapping prescription defined for all breast shapes covered by a breast model.

7. The method according to claim 5, wherein for facilitating the mapping into the pictogram model, registering a coordinate system used to describe positions in the pictogram model with the no-compressed breast shape described by the second shape information item.

8. The method according to claim 1, wherein the step of transforming the second spatial information item into the pictogram information item includes at least one rendering process in respect of the non-compressed breast shape described by the second shape information item.

9. The method according to claim 8, which further comprises performing a dynamic adaptation of the pictogram information item depending on at least one user input, describing a modified rendering parameter, for at least one of rotating, zooming or displacing a pictogram obtained by the rendering process.

10. The method according to claim 1, which further comprises ascertaining descriptors facilitating a representation of the position of the target structure in at least one pictogram as the pictogram information item.

11. The method according to claim 10, wherein the descriptors contain a quadrant, in which the target structure is situated, and/or a directional specification, related to a clock face representation, of the target structure in the pictogram and/or a depth information item in an anterior-posterior direction and/or a distance from a marked point or a marked surface, which is also depicted in the pictogram.

12. The method according to claim 11, wherein use is made of the depth information item related to depth sectors depicted in a distinguishable manner in the pictogram.

13. The method according to claim 1, which further comprises assigning a compressed breast shape in each case to views of the compressed breast.

14. The method according to claim 1, which further comprises ascertaining a reliability value with directional resolution.

15. A method for assisting a diagnosing practitioner with describing a location of at least one target structure in a tomosynthesis image data record of a compressed breast of a patient, the target structure being localized by means of a first spatial information item, which comprises the following steps of:
   ascertaining a first shape information item describing at least one first compressed breast shape in the tomosynthesis image data record;
   determining a second shape information item describing the compressed breast in a non-compressed breast shape, from the first shape information item;
   mapping a position of the at least one target structure from the compressed breast shape and to the non-compressed breast shape using at least the second shape information item for ascertaining a second spatial information item relating to the non-compressed breast shape;
   transforming the second spatial information item into a pictogram information item facilitating an abstracted pictorial representation and/or describing the abstracted pictorial representation, wherein a transformation of the second spatial information item to the pictogram information item contains the mapping of the position, described by the second spatial information item, in the non-compressed breast shape into a pictogram model describing a pictogram breast shape, wherein, for facilitating the mapping into the pictogram model, a coordinate system used to describe positions in the pictogram model is registered with the non-compressed breast shape described by the second shape information item.

16. The method according to claim 15, which further comprises ascertaining the first shape information on a basis of at least one of a segmentation of a breast surface, a detection of a nipple or detection of a pectoral muscle.

17. The method according to claim 15, which further comprising using at least one of a data-driven determination method or a determination method based on a biomechanical simulation for ascertaining the second shape information item.

18. The method according to claim 15, wherein in order to ascertain the second spatial information item, carrying out at least one of a biomechanical simulation of a movement of at least the position, described by the first spatial information item, from the compressed breast shape to the non-compressed breast shape or a thin plate spline transformation on a basis of reference positions which are localizable in both the compressed and non-compressed breast shapes.

19. The method according to claim 15, wherein the transformation of the second spatial information item into the pictogram information item includes at least one rendering process in respect of the non-compressed breast shape described by the second shape information item.

20. The method according to claim 19, wherein there is a dynamic adaptation of the pictogram information item depending on at least one user input, describing a modified rendering parameter, for at least one of rotating, zooming or displacing a pictogram obtained by the rendering process.

21. The method according to claim 15, which further comprises ascertaining descriptors facilitating a representation of the position of the target structure in at least one pictogram as the pictogram information item.

22. The method according to claim 21, wherein the descriptors contain a quadrant, in which the target structure is situated, and/or a directional specification, related to a clock face representation, of the target structure in the pictogram and/or a depth information item in an anterior-posterior direction and/or a distance from a marked point or a marked surface, which is also depicted in the pictogram.

23. The method according to claim 22, wherein use is made of the depth information item related to depth sectors depicted in a distinguishable manner in the pictogram.

24. The method according to claim 15, which further comprises using a cylindrical coordinate system.

25. An apparatus for assisting a diagnosing practitioner with describing a location of at least one target structure in a tomosynthesis image data record of a compressed breast of a patient, the target structure being localized by means of a first spatial information item, said apparatus comprising:
   a receiving interface for receiving the tomosynthesis image data record;
   a computer device, containing:
      an ascertainment unit for ascertaining a first shape information item describing at least one first compressed breast shape in the tomosynthesis image data record;
      a determination unit for determining a second shape information item describing a breast in a non-compressed breast shape from the first shape information item by virtue of, in a case of a plurality of views of the compressed breast contained in the tomosynthesis image data record, a second spatial information item being ascertained for each view, wherein the second spatial information item to be used in the following is ascertained by statistical combination of preliminary spatial information items, with the second spatial information item being ascertained by forming a mean value, weighted by a reliability value assigned to a respective preliminary spatial information item, from the preliminary spatial information items;

a transfer unit for mapping a position of the at least one target structure from the compressed breast shape and to the non-compressed breast shape using at least the second shape information item for ascertaining the second spatial information item relating to the non-compressed breast shape; and a transformation unit for transforming the second spatial information item into a pictogram information item facilitating an abstracted pictorial representation and/or describing the abstracted pictorial representation; and an output interface for outputting the pictogram information item and/or a representation derived therefrom.

26. An apparatus for assisting a diagnosing practitioner with describing a location of at least one target structure in a tomosynthesis image data record of a compressed breast of a patient, the target structure being localized by means of a first spatial information item, said apparatus comprising:

a receiving interface for receiving the tomosynthesis image data record;

a computer device, containing:

an ascertainment unit for ascertaining a first shape information item describing at least one first compressed breast shape in the tomosynthesis image data record;

a determination unit for determining a second shape information item describing the compressed breast in a non-compressed breast shape from the first shape information item;

a transfer unit for mapping a position of the at least one target structure from the compressed breast shape and to the non-compressed breast shape using at least the second shape information item for ascertaining a second spatial information item relating to the non-compressed breast shape; and a transformation unit for transforming the second spatial information item into a pictogram information item facilitating an abstracted pictorial representation and/or describing the abstracted pictorial representation, said transformation unit having a first sub-unit for mapping a position in the non-compressed breast shape, described by the second spatial information item, into a pictogram model describing a pictogram breast shape and a second sub-unit for registering a coordinate system used to describe positions in the pictogram model with the non-compressed breast shape described by the second shape information item for facilitating a mapping into the pictogram model; and an output interface for outputting the pictogram information item and/or a representation derived therefrom.

* * * * *